United States Patent [19]
Qin et al.

[11] Patent Number: 6,129,876
[45] Date of Patent: *Oct. 10, 2000

[54] HEAT SETTING OF MEDICAL TUBINGS

[75] Inventors: Chuan Qin, Gurnee; Patrick T. Ryan, Crystal Lake; Donna Rostron, Bartlett; Birendra K. Lal, Lake Zurich; Yuanpang S. Ding, Vernon Hills; Susan Mizener, Round Lake Heights; Michael T. K. Ling, Vernon Hills; Dean Laurin, Round Lake Beach; Lecon Woo, Libertyville, all of Ill.

[73] Assignee: Baxter International Inc., Deerfield, Ill.

[ * ] Notice: This patent is subject to a terminal disclaimer.

[21] Appl. No.: 08/642,656

[22] Filed: May 3, 1996

[51] Int. Cl.$^7$ .......................... B29C 47/00; B29C 55/06; B29D 23/00

[52] U.S. Cl. ................................... 264/209.5; 264/211.2; 264/235.6; 264/288.4

[58] Field of Search .......................... 264/209.3, 209.4, 264/209.5, 557, 567, 288.4, 342 RE, 235.6, 178 R, 211.12, 211.13

[56] References Cited

U.S. PATENT DOCUMENTS

| | | | |
|---|---|---|---|
| 813,918 | 2/1906 | Schmitz | 122/511 |
| 2,423,260 | 7/1947 | Slaughter | 264/209.3 |
| 2,551,710 | 5/1951 | Slaughter | 240/51.11 |
| 2,919,462 | 1/1960 | Friden | 264/557 |
| 2,940,126 | 6/1960 | Sheridan | 264/557 |
| 3,157,724 | 11/1964 | Salyer et al. | 264/288 |
| 3,218,380 | 11/1965 | Euling et al. | 264/95 |
| 3,260,776 | 7/1966 | Lindstrom, Jr. et al. | 264/95 |

(List continued on next page.)

FOREIGN PATENT DOCUMENTS

| | | |
|---|---|---|
| 250874 | 8/1988 | Czechoslovakia . |
| 0 133 355 A2 | 7/1984 | European Pat. Off. . |
| 0 256 644 | 2/1988 | European Pat. Off. . |
| 0 450 088 A1 | 10/1991 | European Pat. Off. . |
| WO 92/18173 | 10/1992 | European Pat. Off. . |
| 0 573 884 A2 | 2/1993 | European Pat. Off. . |
| 07205275 | 8/1995 | European Pat. Off. . |
| 07205276 | 8/1995 | European Pat. Off. . |
| 1928843 | 12/1990 | Germany . |
| 4332624 | 11/1992 | Japan . |
| WO 80/02671 | 11/1980 | WIPO . |
| WO 93/23093 | 11/1993 | WIPO . |
| WO 94/26793 | 11/1994 | WIPO . |
| WO 96/08520 | 3/1996 | WIPO . |
| WO 96/36374 | 11/1996 | WIPO . |

OTHER PUBLICATIONS

European Plastic News, Jun., 1996; *Medical Tubes Use Metallocene Resin* p. 17.

Feb. 7, 1995, Functionalized Modified High Melt Flow Polyolefins, Wilpers et al., United States Statutory Invention Registration No. H1419.

Aug. 23, 1995, The Effect of Plastic Formulation Variables on Bond Strengths Achieved With Typical Medical Device Adhesives, presented at Manufacturing Medical Plastics 1995 by Pat Courtney, Senior Application Engineer, Loctite Corporation.

Patrick J. Courtney and James Serenson, "Adhesive Bonding of Medical Plastics: An Overview", Jan./Feb. 1996 Medical Plastics and Biomaterials, pp. 20–25.

*Primary Examiner*—Jan H. Silbaugh
*Assistant Examiner*—Mark Eashoo
*Attorney, Agent, or Firm*—Mark J. Buonaiuto; Joseph A. Fuchs

[57] ABSTRACT

The present invention provides a method for fabricating flexible medical tubings comprising the steps of providing a tubing of a polymer material, the tubing having a longitudinal axis and an initial diameter, orienting the tubing along the longitudinal axis of the tubing to reduce the diameter of the tubing to define a oriented diameter, and applying heat to the oriented tubing to heat set the tubing to maintain dimensional stability of the tubing over a temperature to which the tubing will normally be exposed.

13 Claims, 1 Drawing Sheet

U.S. PATENT DOCUMENTS

| | | | |
|---|---|---|---|
| 3,581,776 | 6/1971 | Sheahan | 138/108 |
| 3,775,523 | 11/1973 | Haley | 264/95 |
| 3,856,889 | 12/1974 | McConnell | 260/876 |
| 3,886,227 | 5/1975 | VanBrederode et al. | 260/836 |
| 3,974,240 | 8/1976 | Bock et al. | 260/889 |
| 4,014,369 | 3/1977 | Kobres, Jr. | 138/112 |
| 4,115,495 | 9/1978 | Hartitz | 264/567 |
| 4,152,380 | 5/1979 | Graves et al. | 264/209.4 |
| 4,157,194 | 6/1979 | Takahashi | 285/3 |
| 4,157,235 | 6/1979 | Lagabe et al. | 264/167 |
| 4,193,899 | 3/1980 | Brenner et al. | 264/230 |
| 4,374,882 | 2/1983 | Harlan | 428/36 |
| 4,422,999 | 12/1983 | Mitchell | 264/339 |
| 4,444,817 | 4/1984 | Subramanian | 428/36 |
| 4,613,533 | 9/1986 | Loomis et al. | 428/36 |
| 4,623,567 | 11/1986 | Hert . | |
| 4,678,834 | 7/1987 | Boivin et al. | 575/74 |
| 4,698,196 | 10/1987 | Fabian | 264/565 |
| 4,721,637 | 1/1988 | Suzuki et al. . | |
| 4,737,547 | 4/1988 | White | 525/193 |
| 4,886,634 | 12/1989 | Strutzel et al. | 264/560 |
| 4,906,496 | 3/1990 | Hosono et al. | 428/220 |
| 4,948,643 | 8/1990 | Mueller . | |
| 4,957,974 | 9/1990 | Ilenda et al. | 525/301 |
| 5,018,945 | 5/1991 | D'Silva . | |
| 5,045,620 | 9/1991 | Itaba et al. | 526/348.1 |
| 5,048,572 | 9/1991 | Levine | 138/121 |
| 5,082,613 | 1/1992 | Kasakevich et al. | 264/209.4 |
| 5,096,634 | 3/1992 | Tsadares et al. | 264/40.2 |
| 5,151,019 | 9/1992 | Danby et al. . | |
| 5,169,708 | 12/1992 | Amaral et al. | 428/215 |
| 5,225,451 | 7/1993 | Rogers et al. | 521/94 |
| 5,241,031 | 8/1993 | Mehta | 264/346 |
| 5,264,488 | 11/1993 | Takeuchi et al. | 525/89 |
| 5,274,035 | 12/1993 | Chundary . | |
| 5,281,670 | 1/1994 | Lee et al. | 525/207 |
| 5,343,738 | 9/1994 | Skaggs | 73/40.5 |
| 5,439,454 | 8/1995 | Lo et al. . | |
| 5,447,672 | 9/1995 | O'Neil | 264/209.4 |
| 5,505,900 | 4/1996 | Suwanda et al. | 264/288.4 |
| 5,525,388 | 6/1996 | Wand et al. . | |
| 5,562,127 | 10/1996 | Fanselow et al. | 138/137 |
| 5,573,822 | 11/1996 | Nishikawa et al. . | |
| 5,620,760 | 4/1997 | Galimbert et al. . | |
| 5,629,059 | 5/1997 | Desai et al. . | |
| 5,638,660 | 6/1997 | Kuo . | |
| 5,741,452 | 4/1998 | Ryan et al. | 264/209.5 |
| 5,746,968 | 5/1998 | Radisch, Jr. | 264/529 |

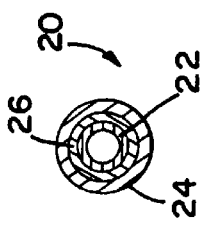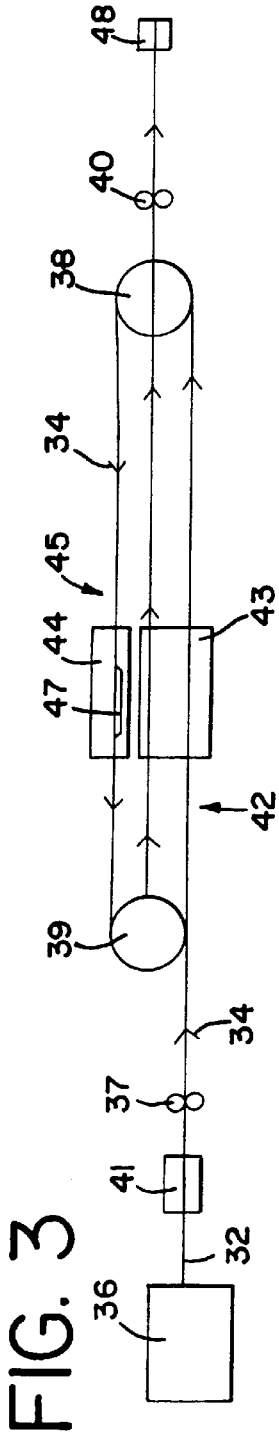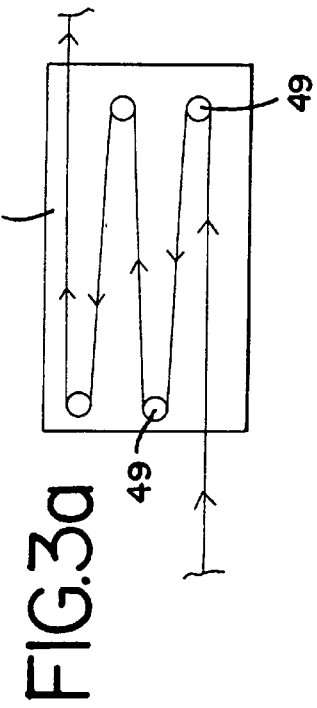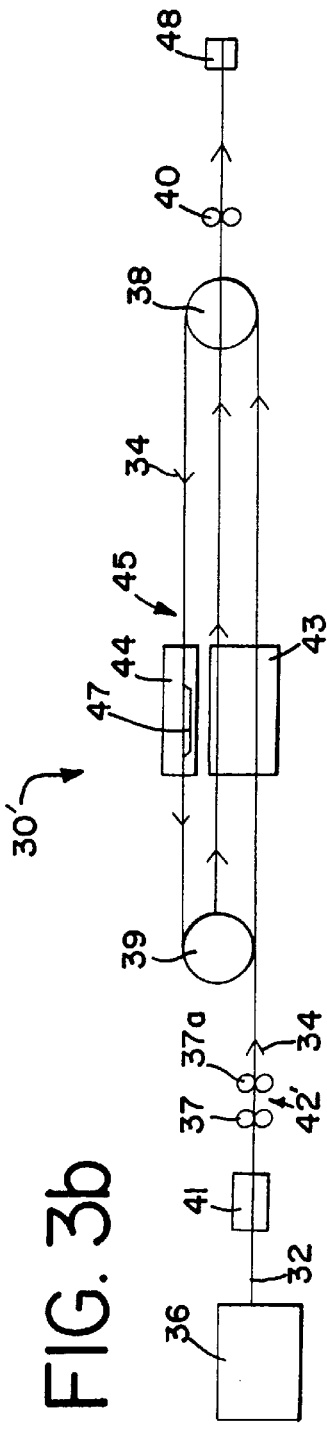

HEAT SETTING OF MEDICAL TUBINGS

TECHNICAL FIELD

This invention relates to a method for fabricating medical tubing and more particularly to a process for heat treating the tubing after the tubing has been oriented along its longitudinal axis to maintain dimensional stability of the tubing.

BACKGROUND ART

In the medical field, where beneficial agents are collected, processed and stored in containers, transported and ultimately delivered through tubes by infusion to patients, there has been a recent trend toward developing materials useful for fabricating such containers and tubing without the disadvantages of currently used materials such as polyvinyl chloride. These new materials for tubings must have a unique combination of properties, so that the tubing may be used in fluid administration sets and with medical infusion pumps. Among these properties are the materials must be optically clear, environmentally compatible, have sufficient yield strength and flexibility, have a minimum quantity of low molecular weight additives, and be compatible with medical solutions.

It is desirable for medical tubing to be optically transparent to allow for visual inspection of fluids in the tubing. Ultrasonic waves must also be capable of passing through the tubing because sensors associated with an infusion pump typically use ultrasonic waves to detect abnormal conditions such as air bubbles in the tubing.

It is also a requirement that the tubing be environmentally compatible as a great deal of medical tubing is disposed of in landfills and through incineration. For tubing disposed of in landfills, it is desirable to use as little material as possible to fabricate the tubing. Further benefits are realized by using a material which is thermoplastically recyclable so that scrap generated during manufacturing may be incorporated into virgin material and refabricated into other useful articles.

For tubing that is disposed of by incineration, it is necessary to use a material that does not generate or minimizes the formation of by-products such as inorganic acids which may be environmentally harmful, irritating, and corrosive. For example, PVC may generate objectionable amounts of hydrogen chloride (or hydrochloric acid when contacted with water) upon incineration, causing corrosion of the incinerator and possible pollution to the environment.

To be compatible with medical solutions, it is desirable that the tubing material be free from or have a minimal content of low molecular weight additives such as plasticizers, stabilizers and the like. These components could be extracted by the therapeutic solutions that come into contact with the material. The additives may react with the therapeutic agents or otherwise render the solution ineffective. This is especially troublesome in bio-tech drug formulations where the concentration of the drug is measured in parts per million (ppm), rather than in weight or volume percentages. Even minuscule losses of the bio-tech drug can render the formulation unusable. Because bio-tech formulations can cost several thousand dollars per dose, it is imperative that the dosage not be changed.

Polyvinyl chloride ("PVC") has been widely used to fabricate medical tubings as it meets most of these requirements. PVC tubing is optically clear to allow for visual inspection of the fluid flowing through it. PVC tubing has proven to work well in pump administration sets. PVC medical tubing also has desirable stress-strain characteristics so that the material may be oriented along a longitudinal axis of the tubing without causing a reduction in the diameter of the tubing. In other words, PVC tubing resists necking. PVC medical tubing also has favorable surface characteristics to allow for controlling the flow rate of fluid through the tubing using slide clamps which operate by crimping the sidewall of the tubing to stop or reduce the flow of fluid through the tubing. The slide clamp may be used without causing scoring or cutting of the tubing.

Because PVC by itself is a rigid polymer, low molecular weight components known as plasticizers must be added to render PVC flexible. As set forth above, these plasticizers may be extracted out of the tubing by the fluid. For this reason, and because of the difficulties encountered in incinerating PVC, there is a need to replace PVC medical tubing.

Polyolefins and polyolefin alloys have been developed which meet many of the requirements of medical containers and tubing, without the disadvantages associated with PVC. Polyolefins typically are compatible with medical applications because they have minimal extractability to fluids. Most polyolefins are environmentally sound as they do not generate harmful degradants upon incineration, and in most cases are capable of being thermoplastically recycled. Many polyolefins are cost effective materials that may provide an economic alternative to PVC. However, there are many hurdles to overcome to replace all the favorable attributes of PVC with a polyolefin.

For example, problems have been encountered in using polyolefins, such as an ultra-low density polyethylene (ULDPE), to fabricate medical tubing. Such tubing has been found to have poor surface characteristics so that it is readily susceptible to cutting, shredding or scoring when clamping the tubing using a slide clamp. ULDPE tubing also presents difficulties during use in pump pressurized administration sets where the pump controls the flow rate of fluid through the tubing by consecutively impinging upon the sidewalls of the tubing to deliver a precise amount of fluid over a given time period.

Pumps that are used to infuse beneficial agents to patients typically have various sensors to detect such conditions as back pressure of fluid in the tubing, and air bubbles in the fluid stream. The sensors deactivate the pump upon detecting an unacceptable back pressure or an air bubble. The sensors usually have a sensor body in which a segment of the tubing of the administration set is secured in place. It has been found that there is a tendency for the polyolefin tubing to deform when placed in the sensor body due to resistance with side walls of the sensor housing. This deformation in some cases leads the detectors to indicate an abnormal condition and to inappropriately deactivate the infusion pump.

Further, polyolefin tubing has been found to have low yield strength and thus are readily susceptible to a phenomenon which is referred to as necking. Necking is a localized reduction in the diameter of the tubing that occurs upon stretching the tubing under moderate strain along the longitudinal axis of the tubing. Necking can cause a reduction or complete restriction in the flow of fluid through the tubing thereby rendering the tubing ineffective. Because there is a linear relationship between yield strength and modulus, it is possible to increase the modulus of the material to increase the yield strength. However, to get a sufficient yield strength for medical applications, the resulting tubing has too high a modulus to function in pumps.

The Applicants have found that it is possible to increase the tubings' resistance to necking by pre-orienting the tubing along the longitudinal axis of the tubing. However, the orientation process may lead to dimensional instability. In particular, oriented polyolefin tubing experiences a phenomenon known as heat recovery, which is sometimes referred as the "memory effect." Heat recovery is a complicated phenomenon that occurs when oriented tubing is heated above the temperature reached during the orientation process. When this occurs the tubing loses its orientation causing shrinking and dimensional changes of the tubing.

Polyolefin tubings have also been shown to have poor thermal stability during storage, transportation, and end applications. The poor thermal stability is thought to be due in part to polyolefins' low melting or crystallization temperatures, low glass transition temperatures, and due to the orientation process referred to above. The poor thermal stability of polyolefin tubings can lead to changes in the desired dimensions and also lead to coiling of the tubing during shipping or use. These dimensional and shape changes can in turn lead to functional problems such as accuracy, pump compatibility, and cause other cosmetic defects.

DISCLOSURE OF INVENTION

The present invention provides a method for fabricating flexible medical tubings comprising the steps of providing a polymeric tubing having a longitudinal axis and an initial diameter, orienting the tubing along the longitudinal axis of the tubing to reduce the diameter of the tubing to define an oriented diameter, and applying heat to the oriented tubing to heat set the tubing to maintain dimensional stability of the tubing. Preferably the initial diameter is 10%–300% greater than the oriented diameter. Preferably the step of orienting the tubing can be done in a wet or a dry process. Each orienting process shares the steps of extending the tubing between a first puller and a second puller spaced apart by a distance and controlling the relative speeds of the first puller and the second puller so that the rate of pulling of the second puller is greater than that of the first puller to orient the tubing therebetween. In the wet orientation process, the tubing is passed through an aqueous bath during the orientation step and in the dry process the tubing is not.

The present invention further provides for heat setting of the tubing to overcome the memory effect discussed above. The heat setting process includes the step of exposing the tubing to a temperature higher than that which the tubing will normally be exposed during shipping, storage, and use, but below the temperature at which the tubing is fully melted. By exposing the tubing to temperatures above the application temperature; less ordered, lower melting crystals are melted leaving higher melting crystals which will be thermally stable over the application temperature range. Part of the highly oriented macro-molecule chains will also be relaxed at heat setting temperatures resulting in a tubing with good thermal stability.

The heat setting step includes the steps of heating the tubing after the orienting step in a heated aqueous bath. Preferably, the tubing is not oriented during the heating step but is held under sufficient tension to prevent the tubing from sagging. It is also possible to allow the tubing a little slack so the tubing may sag slightly. It is also preferable that the tubing be supported with a structure to prevent or minimize further orienting of the tubing.

Finally, it is desirable to position a plurality of spaced rollers in the heating bath. The tubing is trained about the rollers to define a serpentine pattern so that the tubing makes several lengthwise passes through the heating bath. It may be desirable to motorize these rollers.

BRIEF DESCRIPTION OF DRAWINGS

FIG. 1 is an enlarged cross-sectional view of a medical tubing fabricated from a monolayer polymer blend of the present invention;

FIG. 2 is an enlarged cross-sectional view of a multi-layered tubing of the invention;

FIG. 3 is a schematic representation of a method for forming, wet orienting and heat setting medical tubing;

FIG. 3a is a plan view of a serpentine pattern that tubing may follow through a heating or cooling bath of the process shown in FIG. 3; and FIG. 3b is a schematic representation of a method for forming, dry orienting and heat setting medical tubing.

BEST MODE FOR CARRYING OUT THE INVENTION

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

I. POLYMER BLENDS

The polymer blends of the present invention may be embodied in monolayer polymer structures or may be adhered to other substrates such as polymers to form multi-layered structures. The polymer blends of the present invention include a polymeric material and an additive. The polymer blends are capable of being fabricated into medical tubing and attached to rigid polymers.

The polymeric material may be selected from the group consisting of polyolefins and their copolymers, ethylene-propylene rubber, ethylene vinyl acetate copolymers, ethylene methyl acrylate copolymers, styrene and hydrocarbon block copolymers such as styrene-butadiene-styrene or styrene-isoprene-styrene copolymers and their hydrogenated derivatives, thermoplastic elastomers such as polyurethanes, polyamide and polyester copolymers such as those sold under the tradename PEBAX, and copolyesters such as those sold under the tradename HYTREL, polybutadiene, polyisoprene, polyisobutylene, styrene butadiene rubbers, and other cross-linked elastomers.

Suitable polyolefins include both homo and copolymers of polyethylene. Suitable comonomers may be selected from the group consisting of aliphatic olefins, methyl acrylate and vinyl acetate.

Preferably, the polyolefin is an ethylene copolymerized with alpha-olefins including butene-1, octene-1 (collectively referred to as ultra low density polyethylene ("ULDPE")), methyl acrylate (with less than 33% methyl acrylate comonomer), vinyl acetate (with less than 33% methyl acrylate comonomer). ULDPE generally has a density within the range of about 0.8 g/cm$^3$ to about 0.95 g/cm$^3$.

The additive should be a polymer or an aliphatic or aromatic hydrocarbon having greater than 5 carbon atoms in the backbone and further having electron negative groups selected from the group of amines; amides; hydroxyls; acids; acetate, ammonium salts; organometallic compounds such as metal alcoholates, metal carboxylates, and metal complexes of numerous 1,3 dicarbonyl compounds; phenyl phosphines; pyridines; pyrrolidones; imidazoline, and oxazolines.

The blends should have the polymeric component in an amount by weight within the range of 90%–99.999%, more preferably 98.0%–99.99%. The additive should be in an amount by weight within the range of 0.001%–10%, and more preferably 0.01%–2%.

II. METHOD OF BLENDING

The components of the polymer blends should be blended through molten mixing, physical blending such as tumble blending, or other means such as reactive extrusion.

III. METHOD OF FABRICATING MEDICAL TUBING

FIG. 1 shows medical tubing 10 of the present invention fabricated from one of the blends of the present invention. The tubing 10 should have an inner diameter dimension within the range of 0.003–0.4 inches, and an outer diameter dimension within the range of 0.12–0.5 inches. More particularly, medical tubing for use in the administration of fluid using a medical infusion pump, such as Baxter infusion pump sold under the tradename FLO-GARD®, and COLLEAGUE®, have an inner diameter within the range of 0.099–0.105 inches, an outer diameter within the range of 0.134–0.145 inches, and a wall thickness within the range of 0.018–0.021 inches. The tubing should be flexible having a modulus of elasticity of less than 50,000 psi, and more preferably less than 40,000 psi.

FIG. 2 shows a multilayered tubing 20 having a first layer 22, which is a solution contact layer, a second layer 24 and a tie layer 26 therebetween. The first layer 22 may be selected from the same group of polymers set forth above for the polymeric component. The first layer 22, however, will not have the additive. The second layer 24 will be of the blends specified above having a polymeric material and an additive selected from the groups and amounts specified above. In many cases the first layer 22 will be sufficiently compatible with the second layer 24 to do without the tie layer 26.

The first layer 22 of the tube 20 should have a thickness as a percentage of the total wall thickness within the range of 98%–50%, the second layer 24 should have a thickness within the range of 2–50%, and the tie layer 26 should have a thickness within the range of 0–10%.

IV. Method of Heat Setting and Orienting the Tubing

It is also desirable for the tubings 10,20 to be oriented along their longitudinal axes. This orientation step increases the yield strength of the tubing in the longitudinal direction thereby reducing the tendency for the tubing to neck during use. In effect, pre-orienting of the tubing increases the resistance to further necking. Preferably, the tubing 10,20 should be oriented so that the initial inner and outer diameters of the tubing are anywhere from 10%–300% greater than the diameter of the tubing 10,20 after orienting and more preferably from 20%–120% and most preferably from 30%–70% higher. These ranges further include all combinations and subcombinations therein. The ratio of the beginning diameter to the diameter after orienting shall be referred to as the orientation ratio. The orientation process may be a wet orientation process or a dry one as set forth below.

FIG. 3 shows a schematic representation 30 of the method of orienting the tubing in a wet orientation process. The method of wet orienting includes the steps of providing a tubing 32 from a polymeric blend, and orienting the tubing 32 along its longitudinal axis so that the tubing 32 has a desired inner and outer diameter, as specified above in Section III, and orientation ratio. The orienting step orients the molecules of the tubing along the longitudinal axis to increase the resistance to necking upon subsequent longitudinal stressings. The tubing 32 is then heat set to reduce shrinkage of the tubing and to fix the tubing in the oriented dimension.

The tubing 32 (which may be a single layered tubing 10 or a multilayered tubing 20) is pulled in a direction indicated by arrows 34 along a continuous path that may be referred to as a line. The term "up-line" shall refer to locations along the line in a direction opposite the direction to the flow of the tubing 32. Conversely, the term "down-line" shall refer to locations in the direction of the flow of the tubing. By using the term "line" it should not be thought that the method must be carried out in a straight line, rather it should be taken to mean that the method is carried out in a sequence of consecutive steps.

As shown in FIG. 3, tubing 32 is formed with an extruder 36. The tubing 32 exiting the extruder 36 preferably has an outer diameter dimension that will be from 10%–300% greater than after orienting and more preferably from 20%–120%, and most preferably from 30%–70% greater. The diameter of the tubing exiting the extruder 36 shall be referred to as the initial diameter.

The tubing 32 is pulled from the extruder 36 with a first puller 37, a second puller 38, a third puller 39, and a fourth puller 40. The pullers 37, 38, 39 and 40 may have a silicone or rubber coating to increase the coefficient of friction with the tubing 32. The second and third pullers 38 and 39 may have a plurality of axially spaced and circumferentially extending grooves to accommodate more than one set of tubing 32 on a surface of the pullers 38 and 39 at a time.

After exiting the extruder 36, the tubing 32 passes through a first cooling bath 41 where the tubing 32 is cooled with air or a liquid. Preferably, the first cooling bath 41 is a water bath at a temperature within the range of 4° C.–45° C.

After exiting the first cooling bath 41 the tubing 32 extends between the first and second pullers 37 and 38 where the tubing 32 is oriented by operating the second puller 38 at a greater rate of speed than the first puller 37 to achieve the desired orientation ratio. This section of the line will be referred to as the orienting section 42. Preferably the second puller 38 is operated at a rate within the range of about 4–10 times faster than the first puller 37. By controlling the relative speeds of the first and second pullers 37 and 38 one can control the final inner and outer diameters of the tubing 32 and achieve the desired orientation ratio.

In the orienting section 42 the tubing 32 is passed through a second cooling bath 43 where the tubing 32 is cooled with air or a liquid. Preferably, the second cooling bath 43, as the first cooling bath 41, is an aqueous bath at a temperature within the range of 4° C.–45° C.

To overcome the memory effect of the oriented tubing 32, it is necessary to heat the tubing to a temperature above that which it will normally be exposed during shipping, storage and use, but below the temperature at which the tubing is fully melted. By exposing the tubing to temperatures above the application temperature, less ordered lower melting crystals are melted leaving higher melting crystals which will be thermally stable over the application temperature range. Part of the highly oriented macro-molecule chains will be relaxed to provide a tubing with enhanced thermal stability.

Toward this end, after exiting the second cooling bath 43, the tubing 32 trains about the second puller 38 and extends between the second puller 38 and the third puller 39. The tubing 32 proceeds in a direction back toward the extruder 36 and through a heating bath 44 where the tubing is heat set. Preferably, the heat bath 44 is positioned above the second cooling bath 43 to save floor space. However, this positioning is optional. This portion of the process will be referred to as the heat setting section or step 45. Preferably, the heat setting step 45 is done on-line after the orienting section 42, but could be done off-line in a batch mode process. During the heat setting step 45, the tubing 32 is passed through a heating bath 44 where the tubing 32 is heated with a medium such as heated air or liquid. The heating bath 44 preferably is an aqueous solution of water at a temperature of between about 50–99° C. Additives such as salt may be added to the aqueous solution.

It is desirable that the tubing 32 not be oriented during the heat setting step 45. For this reason the tubing 32 should be kept under minimum tension to keep the tubing taught or the tubing should be allowed to sag an amount, between the second and third pullers 38 and 39, to prevent or control the shrinkage. Thus, the second and third pullers 38 and 39 should be operated at similar speeds or puller 39 could be operated at a slightly slower speed than puller 38 to accommodate some shrinkage.

To further prevent orienting of the tubing 32 in the heat setting section 45, it may also be desirable to support the tubing 32 while being pulled through the heating bath 44 with a supporting structure 47. However, providing the supporting structure 47 is optional. Suitable supporting structures 47 include a conveyor that moves at the same rate of speed as the tubing 32 through the heating setting section 45. Another supporting structure 47 is a plastic or metal conduit having a diameter greater than that of the tubing wherein the tubing 32 is supported by the interior surface of the conduit.

After exiting the heating bath 44, the tubing 32 extends between the third puller 39 and the fourth puller 40. Puller 40 should be operated at a similar speed of puller 39 or slightly slower than 39 to prevent further orientation. The tubing 32 is passed again through the second cooling bath 43. Of course it is possible to provide for a separate cooling bath, but this arrangement saves floor space.

It may also be desirable to provide for the tubing 32 to make several lengthwise passes through the cooling bath 43 or heating bath 44 as shown in FIG. 3a to provide for maximum cooling or heating of the tubing in a minimal amount of space. This may be accomplished by providing a plurality of spaced rollers 49 to define a serpentine pattern through the heating bath 44 or cooling bath 43.

To prevent any further orientation of the tubing 32, it may be necessary to operate the fourth puller 40 at a similar speed or slightly slower rate of speed than the third puller 39.

After passing the fourth puller 40, the tubing has an oriented diameter and passes through a cutter or spool 48 where the tubing 32 is cut to the appropriate length or wrapped about the spool for storage or shipment.

FIG. 3b shows a dry orientation process 30'. The dry orientation process is same in most respects to the wet orientation process with the major exception that the tubing 32 is oriented in section 42' between pullers 37 and 37a. Puller 37a is operated at a speed greater than puller 37. During the dry orientation step 42', the tubing 32 is not submerged in the aqueous bath 43 as is the case in the wet orientation step 42. In the dry orientation process, pullers 38, 39, and 40 will be run at a rate similar to or slower than puller 37a.

V. EXAMPLES

A. Example 1

An ultra-low density polyethylene sold under the name EXACT 4011 (Exxon Chemical Company) was fabricated into tubing, oriented to various orientation ratios and heat set. The EXACT 4011, in an amount by weight of 99.77%, was tumble blended with an ETHOMEEN 0/15 (Akzo Nobel Chemical Company) in an amount by weight of 0.23%.

The tubing was fabricated by extruding in a 1.5 inch extruder (Davis Standard). The extrusion conditions were as follows: die pin outer diameter 0.240 inches, and die bushing inner diameter 0.325 inches. Barrel zone Nos. 1–4 temperatures were in degrees fahrenheit, respectively: 425, 428, 422, 425. Die Zone Nos. 1–3 temperatures were, in degrees fahrenheit, respectively: 425, 425, 426.

The tubing exiting the extruder was trained about a series of 5 pullers as schematically set forth in FIG. 3b. Pullers 1–5 were operated at the following respective speeds in feet per minute: 17 FPM, 58 FPM, 41 FPM, 32 FPM, and 33 FPM.

The tubing was passed through heating and cooling baths as schematically shown in FIG. 3b. The heating and cooling bath equipment is a triple pass sizing/cooling system sold by Vulcan under model No. CS60STI. The temperature of the heat setting bath varied as set forth in Table I below. The heating bath has a series of rollers as set forth in FIG. 3b so that the tubing was in the heating bath for 13 seconds.

Tubing made in accordance with the above conditions was subjected to shrinkage tests. The tubing length was measured and recorded for each group of tubings. Tubing samples were then placed in a conditioning oven at 150° F. and 50% relative humidity for 1 hour. Tubing samples were then removed and allowed to cool to ambient temperature. The samples were measured for length and recorded. The percentage change in length was calculated as set forth in Table I.

Tensile strength tests were also conducted on other samples of the tubing. The inner, and outer diameter of the tubing and the tubing wall thickness was measured using a LaserMike 183 Benchtop Optical Micrometer. The samples were then tested with an Instron 4201 tester with a crosshead speed of 20 inches per minute. Stress at 100% elongation was used to represent the Yield of the tubing in psi as reported in Table I.

Exact 4011 was also extruded under similar conditions and formed into tubing without the heat set process.

The results set forth in Table I show an improved change in dimensional stability and yield with heat set and oriented tubing as compared to non-heat set tubing. The shrinkage is measured as a percentage change from the initial length before being placed in the oven and the final length after being removed from the oven.

TABLE I

| TUBING COMP. | Temp. (° C. of heat bath) | Shrinkage | Yield |
|---|---|---|---|
| Exact 4011 | n/a | 21.88 | 920 |
| Exact 4011 and Ethomeen | 73 | 5.38 | 1100 |
| | 74 | 3.00 | 1030 |
| | 75 | 2.54 | 970 |
| | 76 | 2.33 | 950 |
| | 77 | 1.60 | 850 |
| | 78 | 0.49 | 820 |

TABLE I-continued

| TUBING COMP. | Temp. (° C. of heat bath) | Shrinkage | Yield |
|---|---|---|---|
| | 79 | 1.37 | 770 |
| | 80 | 0.19 | 730 |

B. Example 2

The procedure for fabricating tubing and testing the tubing as set forth in Example 1 was repeated with slightly different operating conditions to produce a sample of tubing from a blend of ethylene vinyl acetate (EVA) (UE-634, Quantum Chemical Corporation) with Ethomeen 0/15 (0.23% by weight) (Akzo Nobel Chemical Company). Tubing samples were also prepared from pure EVA of the same type in the blend.

The barrel zone temperature for zone Nos. 1–4 were respectively as follows in degrees fahrenheit: 374, 375, 378, and 375. Die zone temperature for zone Nos. 1–3 were as follows in degrees fahrenheit: 375, 375, 376. The puller speeds of pullers Nos. 1–5 were respectively as follows in feet per minute: 17, 60, 41, 31, and 31.5.

The dimensional stability and Yield strength data are set forth below in Table II.

TABLE II

| Tubing Comp. | Temp. (° C. of heat bath) | Shrinkage | Yield |
|---|---|---|---|
| EVA | n/a | 10.00 | 925 |
| EVA and | 70 | 4.09 | 560 |
| Ethomeen | 71 | 1.83 | 550 |
| | 72 | 1.67 | 595 |
| | 73 | 1.60 | 520 |
| | 74 | 1.23 | 490 |
| | 75 | 1.23 | 510 |
| | 76 | 1.11 | 480 |
| | 77 | 1.49 | 500 |
| | 78 | 1.76 | 510 |

C. Example 3

The procedure for fabricating tubing and testing the tubing as set forth in Example 1 was repeated with slightly different operating conditions to produce a sample of tubing from a blend of an ultra-low density polyethylene (ULDPE) sold by the Dow Chemical Company under the name Dow Affinity VP1770, and Ethomeen 0/15 (0.23% by weight) (Akzo Nobel Chemical Company). Another sample of tubing was formed from Dow Affinity ULDPE alone.

The barrel zone temperature for zone Nos. 1–4 were respectively as follows in degrees fahrenheit: 424, 425, 422, and 425. Die zone temperature for zone Nos. 1–3 were as follows in degrees fahrenheit: 425, 425, 425. The puller speeds of pullers Nos. 1–5 were respectively as follows in feet per minute: 17, 60, 41, 31, and 31.5.

The dimensional stability and Yield strength data are set forth below in Table III.

TABLE III

| Tubing Comp. | Temp. (° C. of heat bath) | Shrinkage | Yield |
|---|---|---|---|
| VP 1770 | n/a | 23.75 | 2400 |
| VP 1770 | 74 | 4.86 | 1140 |
| and Ethomeen | 75 | 4.34 | 1120 |
| | 76 | 3.96 | 1150 |
| | 77 | 3.95 | 1100 |
| | 78 | 3.08 | 1090 |
| | 79 | 2.03 | 1070 |
| | 80 | 1.11 | 1000 |
| | 81 | 0.86 | 1030 |
| | 82 | 0.43 | 900 |
| | 83 | 0.31 | 870 |
| | 84 | 0.62 | 800 |
| | 85 | 1.00 | 770 |
| | 86 | 1.13 | 760 |
| | 86 | 1.01 | 720 |

D. Example 4

Tubing samples were also produced in a similar orientation process set forth above in Examples 1–3. One set of tubing samples was oriented to a 50% orientation ratio. A second sample was not oriented. The tubing was made from the constituents set forth below in Table IV, namely, Exact 4011, EVA, and VP1770. The necking resistance of the tubing was measured by initially measuring the inner and outer diameters, and length of the tubing. One end of the tubing was clamped. A Catillon gauge was attached to the opposite end of the tubing. The Catillon gauge exerted a 5 lb. force longitudinally on the tubing for 10 seconds. Afterwards, the tubing was allowed to sit for 5 minutes. The tubing dimensions were measured again and compared with the initial dimension measurements. The percent change in the length dimension is set forth below in Table IV.

TABLE IV

| Tubing Composition | Percent change in length |
|---|---|
| Exact 4011 | 28.45 |
| Exact 4011 (50% orientation) | 0.73 |
| EVA | 15.35 |
| EVA (50% orientation) | 0.72 |
| VP 1770 | 11.42 |
| VP 1770 (50% orientation) | 0.83 |

E. Example 5

An ultra-low density polyethylene Exact 4011 was produced into tubing having an outer diameter within the range of 0.139–0.145 inches and an inner diameter within the range of 0.101–0.105 inches. One sample of the tubing was oriented to a 50% orientation ratio and a second sample of the tubing was oriented to a 35% orientation ratio. Samples of the tubing that were oriented to a 50% orientation ratio were separately submerged in a water bath at 65° C., and 70° C. for 10 seconds and 85° C. for 5 seconds with opposite ends of the tubing clamped to prevent movement or shrinkage of the tubing. After the exposure to the heat the tubing was unclamped and the length of the tubing was measured after cooling in ambient temperature water for 5 minutes. The percent difference in the change of the length of the tubing is reported in Table V below.

The tubing was then placed into an oven at 57° C. for 4 hours. The length after heating was measured and compared to the length before being placed in the oven. The percent difference in length was noted in Table V below.

The other sample of tubing of 35% orientation was not heat treated in a water bath. The non-heat treated tubing was placed in the oven and the percent difference in the length was noted. The results reported in Table V shows that the heat setting step greatly reduces the tendency for the tubing to shrink.

TABLE V

| Temperature of Heat Set (° C.) | Time in Heat Set (Sec.) | % Change in Length (before oven) | % Change in Length (after oven) |
|---|---|---|---|
| 65 | 10 | 1.46 | −3.48 |
| 70 | 10 | 3.75 | −1.40 |
| 85 | 5 | 0 | −0.63 |
| None | NA | NA | −21.9 |

While specific embodiments have been illustrated and described, numerous modifications are possible without departing from the spirit of the invention, and the scope of protection is only limited by the scope of the accompanying claims.

We claim:

1. A method for fabricating flexible medical tubings comprising the steps of:

providing an initial tubing of a polymer material, the initial tubing having a longitudinal axis and an initial diameter;

orienting the initial tubing along the longitudinal axis to reduce the diameter of the initial tubing and thereby produce an oriented tubing having an oriented diameter; and applying heat to the entire oriented tubing to heat set the oriented tubing to maintain dimensional stability.

2. The tubing of claim 1 wherein the initial diameter of the tubing is within a range of 10%–300% greater than the oriented diameter.

3. The method of claim 1 wherein the polymer material is a blend of a polymeric material and an additive wherein the polymeric material is selected from the group consisting of polyolefins and their copolymers, ethylene-propylene rubber, ethylene vinyl acetate copolymers, ethylene methyl acrylate copolymers, styrene and hydrocarbon block copolymer, hydrogenated derivatives of styrene and hydrocarbon block copolymers, thermoplastic elastomers, polyurethanes, polyamide and polyester copolymers, copolyesters, polybutadiene, polyisoprene, polyisobutylene, styrene-butadiene rubbers, and cross-linked elastomers.

4. The method of claim 1 wherein the step of orienting the initial tubing comprises the steps of:

pulling the initial tubing from an extruder at a first rate with a first puller;

pulling the initial tubing from the first puller at a second rate to a position spaced a distance from the first puller with a second puller; and controlling the relative first and second rates so that the second rate of pulling is greater than the first rate of pulling to thereby orient the tubing between the first puller and the second puller.

5. The method of claim 4 further comprising the step of:

cooling the initial tubing during the step of orienting the initial tubing.

6. The method of claim 5 wherein the step of cooling the initial tubing during the step of orienting the initial tubing comprises the steps of:

providing a first fluid bath at a temperature within a range of 4°–45° C.; and passing the initial tubing through the first fluid bath.

7. The method of claim 1 wherein the heat setting step comprises the steps of:

heating the oriented tubing after the orienting step; and cooling the oriented tubing after the heating step.

8. The method of claim 7 wherein the step of heating the oriented tubing includes the step of:

providing a heating bath having a heating medium with a temperature within a range of about 50–99° C.; and pulling the oriented tubing through the heating bath.

9. The method of claim 8 wherein the heating medium is a fluid.

10. The method of claim 8 wherein the heating bath has a lengthwise dimension and wherein the step of heating the oriented tubing includes the steps of:

providing a plurality of spaced rollers in the heating bath; and training the oriented tubing about the rollers to define a serpentine pattern such that the oriented tubing makes several lengthwise passes through the heating bath.

11. The method of claim 10 wherein the rollers are motorized.

12. The method of claim 1 further comprising the step of:

supporting the oriented tubing during the step of applying heat to the oriented tubing.

13. The method of claim 1 further comprising the step of:

extending the oriented tubing between two pullers without further orienting the oriented tubing during the step of applying heat to the oriented tubing.

* * * * *